US011446226B2

(12) United States Patent
Shim et al.

(10) Patent No.: US 11,446,226 B2
(45) Date of Patent: Sep. 20, 2022

(54) COMPOSITION FOR PREVENTING OR IMPROVING INTRINSIC AGING COMPRISING PAEONIFLORIN OR ALBIFLORIN

(71) Applicant: Amorepacific Corporation, Seoul (KR)

(72) Inventors: Jin Sup Shim, Yongin-si (KR); Eun Jung Lee, Yongin-si (KR); Nok Hyun Park, Yongin-si (KR); Yong Jin Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 38 days.

(21) Appl. No.: 16/765,349

(22) PCT Filed: Nov. 22, 2018

(86) PCT No.: PCT/KR2018/014401
§ 371 (c)(1),
(2) Date: May 19, 2020

(87) PCT Pub. No.: WO2019/107831
PCT Pub. Date: Jun. 6, 2019

(65) Prior Publication Data
US 2020/0352842 A1   Nov. 12, 2020

(30) Foreign Application Priority Data
Nov. 30, 2017  (KR) ........................ 10-2017-0163090

(51) Int. Cl.
*A61K 31/7048* (2006.01)
*A61K 8/60* (2006.01)
*A23L 33/105* (2016.01)
*A23L 2/52* (2006.01)
*A61Q 19/08* (2006.01)

(52) U.S. Cl.
CPC .................. *A61K 8/60* (2013.01); *A23L 2/52* (2013.01); *A23L 33/105* (2016.08); *A61K 31/7048* (2013.01); *A61Q 19/08* (2013.01); *A23V 2002/00* (2013.01)

(58) Field of Classification Search
None
See application file for complete search history.

(56) References Cited

U.S. PATENT DOCUMENTS

| 2003/0232102 A1* | 12/2003 | Zhao ...................... A61K 36/65 424/778 |
| 2009/0275527 A1* | 11/2009 | Park ........................ A61P 17/00 514/27 |
| 2012/0270820 A1* | 10/2012 | Zhang .................. A61K 9/4866 514/27 |
| 2017/0112741 A1* | 4/2017 | Torii ...................... A61P 17/08 |

FOREIGN PATENT DOCUMENTS

| CN | 103584093 B | 5/2016 |
| KR | 10-2005-0107649 A | 11/2005 |
| KR | 10-2006-0014714 A | 2/2006 |
| KR | 10-2008-0076999 A | 8/2008 |
| KR | 10-2009-0035274 A | 4/2009 |
| KR | 10-1676601 B1 | 11/2016 |
| KR | 10-2017-0051078 A | 5/2017 |
| WO | 2007/067536 A1 | 6/2007 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Hu, Z. Y., Liu, G., Cheng, X. R., Huang, Y., Yang, S., Qiao, S. Y., . . . & Zhang, Y. X. (2012). JD-30, an active fraction extracted from Danggui-Shaoyao-San, decreases β-amyloid content and deposition, improves . . . Experimental gerontology, 47(1), 14-22. (Year: 2012).*
Chen, S. Q., Lin, J. P., Zheng, Q. K., Chen, S. J., Li, M., Lin, X. Z., & Wang, S. Z. (2015). Protective effects of paeoniflorin against FasL-induced apoptosis of intervertebral disc annulus fibrosus . . . Experimental and therapeutic medicine, 10(6), 2351-2355. (Year: 2015).*
Kim, M. K., Bang, C. Y., Yun, G. J., Kim, H. Y., Jang, Y. P., & Choung, S. Y. (2016). Anti-wrinkle effects of Seungma-Galgeun-Tang as evidenced by the inhibition of matrix metalloproteinase-I . . . BMC complementary and alternative medicine, 16(1), 1-9. (Year: 2016 ).*
W. G. Cho et al., "Stability of Paeoniflorin used as Anti-wrinkle Agents in Emulsions", Journal of the Korean Oil Chemistry Society, Jun. 2009, vol. 26, No. 2, pp. 191-198.
Y. R. Helfrich et al., "Overview of Skin Aging and Photoaging", Dermatology Nursing, Jun. 2008, vol. 20, No. 3, pp. 177-183.
International search report in English for International Application PCT/KR20I8/014401 dated May 10, 2019.
International written opinion in Korean for International Application PCT/KR20I8/014401 dated May 10, 2019.
Zhu Ying-Li et al., "Comparative study on effects of blood enriching on mouse model of blood deficiency syndrome induced by cyclophosphamide of albiflorin, paeoniflorin on levels of GM-CSF, IL-3 and TNF-α", Beijing University of Chinese Medicine and Pharmacology, 2015, vol. 40, No. 2, pp. 323-327 (8 pages).
Office Action dated Jul. 20, 2022, issued in Chinese Application No. 201880076602.1.

* cited by examiner

Primary Examiner — Dale R Miller
(74) Attorney, Agent, or Firm — Sughrue Mion, PLLC

(57) ABSTRACT

The present specification discloses a composition for preventing or improving intrinsic aging comprising, as an active ingredient, any one of paeoniflorin or a salt, isomer, hydrate or solvate thereof; and albiflorin or a salt, isomer, hydrate or solvate thereof. Intrinsic aging is one of the natural phenomena occurring with aging, unlike photoaging caused by UV, which is a type of extrinsic aging. The paeoniflorin or albiflorin of the present disclosure is useful for those who want to delay aging and maintain beauty. Accordingly, the paeoniflorin or a salt, isomer, hydrate or solvate thereof; and the albiflorin or a salt, isomer, hydrate or solvate thereof of the present disclosure have the advantage of being capable of being utilized in various forms such as cosmetics, functional health foods, etc.

6 Claims, 3 Drawing Sheets

COMPOSITION FOR PREVENTING OR IMPROVING INTRINSIC AGING COMPRISING PAEONIFLORIN OR ALBIFLORIN

CROSS-REFERENCE TO RELATED APPLICATION

This is a national stage of PCT International Application No. PCT/KR2018/014401, filed on Nov. 22, 2018, claiming priority based on Korean Patent application No. 10-2017-0163090, filed on Nov. 30, 2017, and all the benefits accruing therefrom under 356 U.S.C. § 119, the contents of which in its entirety are herein incorporated by reference.

TECHNICAL FIELD

The present disclosure relates to a composition for preventing or improving intrinsic aging.

BACKGROUND ART

Aging is classified into intrinsic aging and extrinsic aging. The mechanisms of the two aging processes have not been studied clearly in molecular levels. However, with the finding that the skin conditions, particularly skin wrinkles or skin pigmentation, are different in indoor laborers and outdoor laborers, intrinsic aging and extrinsic aging are being studied distinctively. Intrinsic aging, also known as physiological aging, is natural aging occurring with time. In contrast, extrinsic aging is generally caused by environmental factors. More specifically, photoaging is caused by exposure to sunlight, light or other radiation. For indoor laborers, skin aging occurs mainly due to intrinsic aging rather than extrinsic aging.

The change in skin resulting from intrinsic aging is a result of a genetically programmed sequence involving intrinsic factors. The intrinsic aging reduces the regeneration of skin cells, which leads to clinically impaired appearance such as decreased subcutaneous fat tissue as well as formation of fine wrinkles. In addition, it is accompanied by histopathological changes such as increased number and thickness of elastic fibers, loss of soft tissue fibers from the elastic tissue membrane and formation of large irregular fibroblasts from the elastic tissue.

In contrast, the extrinsic aging leads to clinically impaired appearance such as thickened wrinkles as well as drooping and pigmented skin, and is accompanied by histopathological changes such as excessive accumulation of elastic materials in the upper dermis and degradation of collagen fibers.

Accordingly, the intrinsic aging and the extrinsic aging need to be prevented or improved distinctively. For instance, although a UV-screening agent exhibits an effect of preventing or improving extrinsic aging by protecting the skin from sunlight, thereby preventing photoaging of the skin, it exhibits no effect of preventing or improving intrinsic aging.

Therefore, the inventors of the present disclosure have sought for a method capable of preventing or improving intrinsic aging fundamentally, and have completed the present disclosure by identifying that paeoniflorin and albiflorin are effective in preventing or improving intrinsic aging.

REFERENCES OF RELATED ART

Patent Documents (Patent document 1) Korean Patent Publication No. KR 10-2008-0076999.

Non-Patent Documents (Non-patent document 1) Helfrich, Yolanda Rosi, Dana L. Sachs, and John J. Voorhees. "Overview of skin aging and photoaging." *Dermatology Nursing* 20.3 (2008): 177.

DISCLOSURE

Technical Problem

In an aspect, the present disclosure is directed to providing a composition for preventing or improving intrinsic aging, which contains one or more of paeoniflorin or a salt, isomer, hydrate or solvate thereof, and albiflorin or a salt, isomer, hydrate or solvate thereof as an active ingredient.

Technical Solution

In an aspect, the present disclosure provides a composition for preventing or improving intrinsic aging, which contains one or more of paeoniflorin or a salt, isomer, hydrate or solvate thereof, and albiflorin or a salt, isomer, hydrate or solvate thereof as an active ingredient.

In an aspect, the present disclosure provides a method for preventing or improving intrinsic aging, comprising administering one or more of paeoniflorin or a salt, isomer, hydrate or solvate thereof, and albiflorin or a salt, isomer, hydrate or solvate thereof to a subject in need thereof.

In an aspect, the present disclosure provides a use of one or more of paeoniflorin or a salt, isomer, hydrate or solvate thereof, and albiflorin or a salt, isomer, hydrate or solvate thereof in manufacture of a composition for preventing or improving intrinsic aging.

In an aspect, the present disclosure may provide one or more of paeoniflorin or a salt, isomer, hydrate or solvate thereof, and albiflorin or a salt, isomer, hydrate or solvate thereof for use in preventing or improving intrinsic aging.

In another aspect, the present disclosure provides a composition for preventing or improving intrinsic aging, wherein the composition is a cosmetic composition.

In another aspect, the present disclosure provides a composition for preventing or improving intrinsic aging, wherein the composition is a functional health food composition.

Advantageous Effects

In an aspect, paeoniflorin or a salt, isomer, hydrate or solvate thereof, and albiflorin or a salt, isomer, hydrate or solvate thereof of the present disclosure prevents or improves intrinsic aging. Intrinsic aging is one of the natural phenomena occurring with aging, unlike photoaging caused by UV, which is a type of extrinsic aging. The paeoniflorin or albiflorin of the present disclosure is useful for those who want to delay aging and maintain beauty. Accordingly, the paeoniflorin or a salt, isomer, hydrate or solvate thereof, and the albiflorin or a salt, isomer, hydrate or solvate thereof of the present disclosure have the advantage of being capable of being utilized in various forms such as cosmetics, functional health foods, etc.

BEST MODE

Figure 1:
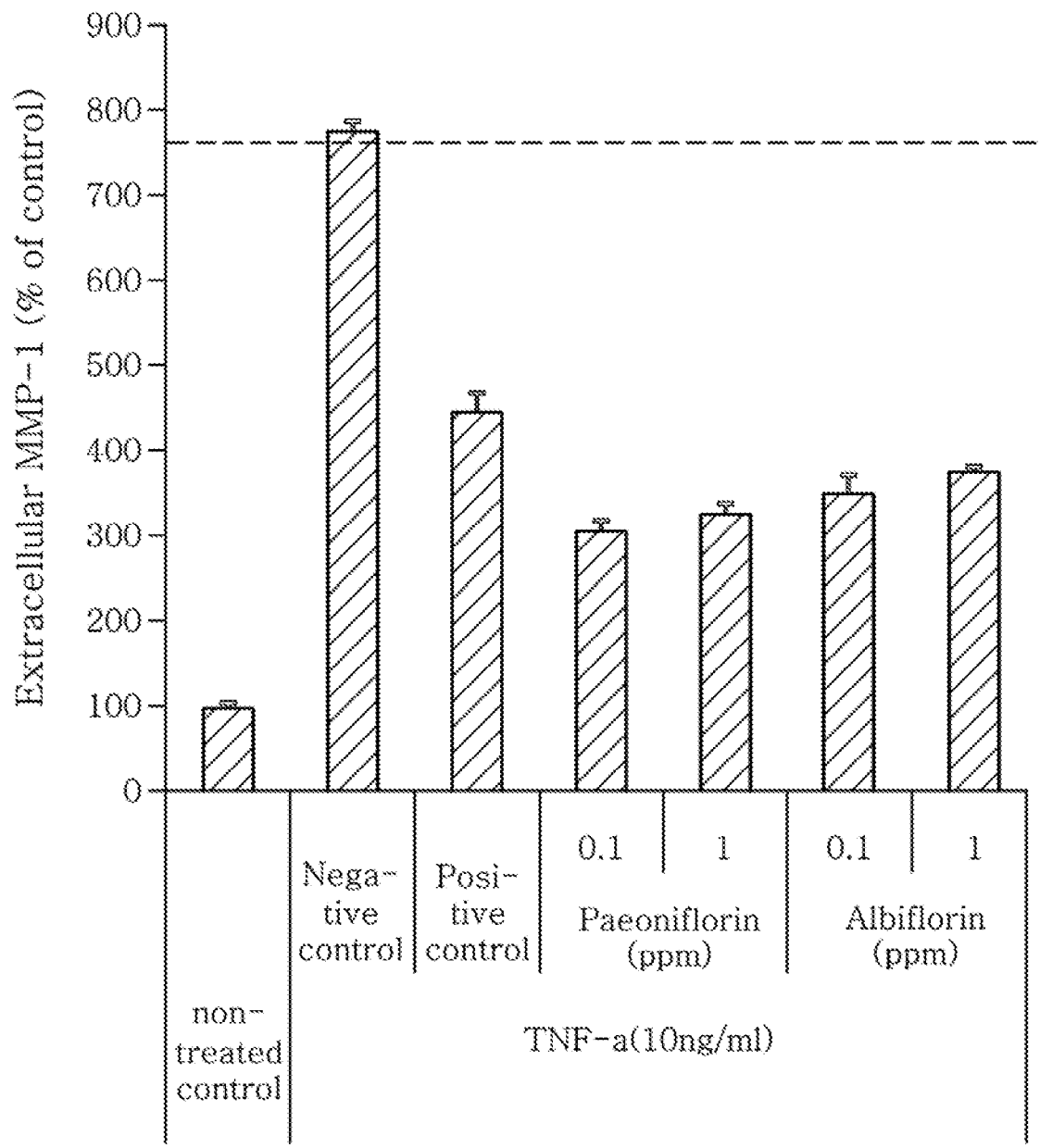
FIG. 1 shows a result of investigating the MMP-1 inhibition effect by paeoniflorin or albiflorin by using TNF-α as a stimulation source.

In an aspect, the present disclosure provides a composition for preventing or improving intrinsic aging, which contains one or more of paeoniflorin or a salt, isomer, hydrate or solvate thereof, and albiflorin or a salt, isomer, hydrate or solvate thereof as an active ingredient.

A detailed description is given hereinafter.

In the present disclosure, 'paeoniflorin' is a substance with a molecular formula of $C_{23}H_{28}O_{11}$ and a molecular weight of 480, and is represented by Chemical Formula 1.

[Chemical Formula 1]

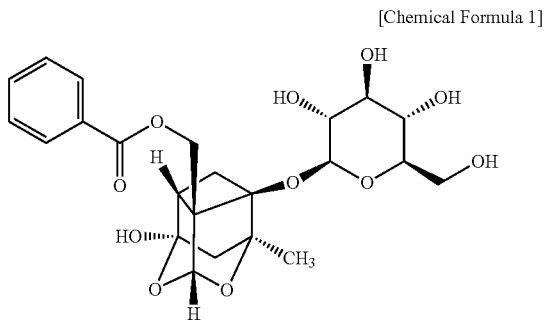 [SMILES: C[C@@]12C[C@@]3(O)O[C@@H](O1)[C@]1(COC(=O)c4ccccc4)[C@H]3C[C@@]12O[C@@H]1O[C@H](CO)[C@@H](O)[C@H](O)[C@H]1O]

In the present disclosure, 'albiflorin' is a substance with a molecular formula of $C_{23}H_{28}O_{11}$ and a molecular weight of 480, and is represented by Chemical Formula 2.

[Chemical Formula 2]

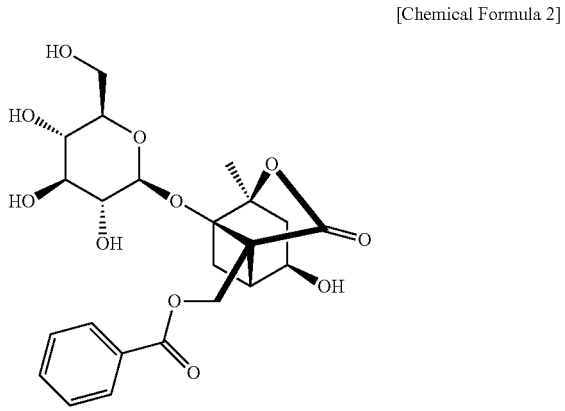

In the present disclosure, 'pharmaceutically acceptable' means being approve or approvable by the government or equivalent regulatory agencies for use in animals, more specifically in human, by avoiding significant toxic effects when used with conventional medicinal dosage, or being recognized as being listed in the pharmacopoeia or described in other general pharmacopoeia.

In the present disclosure, a 'salt', particularly a 'pharmaceutically acceptable salt', includes any organic or inorganic addition salt of paeoniflorin or albiflorin which is relatively nontoxic and innocuous to an individual at concentrations providing effective activity so that the side effects ascribable to the salt do not vitiate the beneficial effects of paeoniflorin or albiflorin, and includes any salt having acidic or basic groups that may be present on paeoniflorin or albiflorin. It includes an acid addition salt formed from a pharmaceutically acceptable free acid or a metal salt formed from a base.

As the free acid, an inorganic acid or an organic acid may be used. As the inorganic acid, hydrochloric acid, hydrobromic acid, bromic acid, sulfuric acid, sulfurous acid, nitric acid, phosphoric acid, etc. may be used. As the organic acid, acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2, 2,2]-oct-2-ene-1-carboxylic acid, glucoheptonic acid, 3-pheylpropionic acid, trimethylacetic acid, tert-butylacetic acid, lauryl sulfuric acid, gluconic acid, glutamic acid, hydroxynaphthoic acid, salicylic acid, stearic acid, muconic acid, etc. may be used. As the metal salt, an alkali metal salt or an alkaline earth metal salt such as sodium, potassium or calcium salts may be used.

In the present disclosure, an 'isomer' includes not only optical isomers, i.e., essentially pure enantiomers, essentially pure diastereomers or mixtures thereof, but also conformational isomers, i.e., isomers differently only in the angle of one or more chemical bonds, position isomers, particularly tautomers, or geometric isomers (e.g., cis-trans isomers).

The expression "essentially pure" means, when used, for example, with regard to enantiomers or diastereomers, that specific compounds, e.g., enantiomers or diastereomers, are present in an amount of about 90% (w/w) or more, specifically about 95% or more, more specifically about 97% or more or about 98% or more, further more specifically about 99% or more, even more specifically about 99.5% or more.

In the present disclosure, a 'hydrate' refers to a compound to which water is bound, and is used in a broad concept, including an inclusion compound with no chemical bonding between water and the compound.

In the present disclosure, 'solvate' refers to a higher-order compound produced from a solute molecule or ion and a solvent molecule or ion.

The paeoniflorin or a salt, isomer, hydrate or solvate thereof, and the albiflorin or a salt, isomer, hydrate or solvate thereof may be purchased commercially or may be isolated and purified from an extract or a fraction of a plant belonging to the family Paeoniaceae, such as peony, tree peony, etc. Although the extract or fraction of a plant belonging to the family Paeoniaceae, such as peony, tree peony, etc. contains paeoniflorin or a salt, isomer, hydrate or solvate thereof, or albiflorin or a salt, isomer, hydrate or solvate thereof, the composition or content of the substances is not constant. Therefore, one or more of paeoniflorin or a salt, isomer, hydrate or solvate thereof, and albiflorin or a salt, isomer, hydrate or solvate thereof, which are compounds obtained through purification and isolation from the extract or fraction may be used as the active ingredient of the present disclosure.

In an exemplary embodiment, in order to seek a synergistic effect derived from combination of the active ingredients, both the paeoniflorin or a salt, isomer, hydrate or solvate thereof and the albiflorin or a salt, isomer, hydrate or solvate thereof may be used as the active ingredients. For instance, the albiflorin or a salt, isomer, hydrate or solvate thereof may be used in an amount of 1 or more, 2 or more, 3 or more, 4 or more, 5 or more, 6 or more, 7 or more, 8 or more, 9 or more or 10 or more, and 11 or less, 12 or less, 13 or less, 14 or less, 15 or less, 16 or less, 17 or less, 18 or less, 19 or less, 20 or less, 21 or less, 22 or less, 23 or less, 24 or less, 25 or less, 26 or less, 27 or less, 28 or less, 29 or less or 30 or less parts by weight, specifically 1-30 parts by weight, more specifically 5-15 parts by weight, based on 100 parts by weight of the paeoniflorin or a salt, isomer, hydrate or solvate thereof, although not being limited thereto.

In the present disclosure, 'intrinsic aging', also known as physiological aging, is natural aging occurring with time and is a result of a genetically programmed sequence. In contrast, extrinsic aging is generally caused by environmental factors. More specifically, photoaging is caused by exposure to sunlight, light or other radiation.

The intrinsic aging reduces the regeneration of skin cells, which leads to clinically impaired appearance such as decreased subcutaneous fat tissue as well as formation of fine wrinkles. In addition, it is accompanied by histopathological changes such as increased number and thickness of elastic fibers, loss of soft tissue fibers from the elastic tissue membrane and formation of large irregular fibroblasts from the elastic tissue.

In an exemplary embodiment, the intrinsic aging may be aging caused by intrinsic inflammation, particularly intrinsic inflammation by TNF-$\alpha$. In addition, the intrinsic aging of the present disclosure includes any intrinsic aging that may be caused by the increase of TNF-$\alpha$, which is an inflammatory factor, in the body. That is to say, in an exemplary embodiment, the intrinsic aging of the present disclosure may be aging caused by TNF-$\alpha$.

In the present disclosure, 'prevention' refers to any action of preventing intrinsic aging or delaying the onset of intrinsic aging by administering a composition.

In the present disclosure, 'improvement' refers to any action of making skin look younger by reducing skin wrinkles caused by intrinsic aging or improving skin elasticity by administering a composition.

Intrinsic aging and extrinsic aging need to be approached in different ways for prevention or improvement. For example, the prevention or improvement of intrinsic aging according to the present disclosure may be achieved by MMP-1 inhibition, although not being limited thereto.

Determination of the administration dosage of the paeoniflorin or a salt, isomer, hydrate or solvate thereof, or the albiflorin or a salt, isomer, hydrate or solvate thereof is within the level of those skilled in the art. A daily dosage may be 0.001 mg/kg/day or more, 0.002 mg/kg/day or more, 0.003 mg/kg/day or more, 0.004 mg/kg/day or more, 0.005 mg/kg/day or more, 0.006 mg/kg/day or more, 0.007 mg/kg/day or more, 0.008 mg/kg/day or more, 0.009 mg/kg/day or more, 0.01 mg/kg/day or more, 0.02 mg/kg/day or more, 0.03 mg/kg/day or more, 0.04 mg/kg/day or more, 0.05 mg/kg/day or more, 0.06 mg/kg/day or more, 0.07 mg/kg/day or more, 0.08 mg/kg/day or more, 0.09 mg/kg/day or more, 0.1 mg/kg/day or more, 0.2 mg/kg/day or more, 0.3 mg/kg/day or more, 0.4 mg/kg/day or more, 0.5 mg/kg/day or more, 0.6 mg/kg/day or more or 0.7 mg/kg/day or more, and 0.8 mg/kg/day or less, and 0.9 mg/kg/day or less, 1 mg/kg/day or less, 1.1 mg/kg/day or less, 1.2 mg/kg/day or less, 1.3 mg/kg/day or less, 1.4 mg/kg/day or less, 1.5 mg/kg/day or less, 1.6 mg/kg/day or less, 1.7 mg/kg/day or less, 1.8 mg/kg/day or less, 1.9 mg/kg/day or less, 2 mg/kg/day or less, 2.1 mg/kg/day or less, 2.2 mg/kg/day or less, 2.3 mg/kg/day or less, 2.4 mg/kg/day or less, 2.5 mg/kg/day or less, 2.6 mg/kg/day or less, 2.7 mg/kg/day or less, 2.8 mg/kg/day or less, 2.9 mg/kg/day or less, 3 mg/kg/day or less, 4 mg/kg/day or less, 5 mg/kg/day or less, 6 mg/kg/day or less, 7 mg/kg/day or less, 8 mg/kg/day or less, 9 mg/kg/day or less or 10 mg/kg/day or less, although not being limited thereto. The administration dosage will vary depending on various factors such as the age and health condition of a subject, presence of complication(s), etc.

In another aspect, the present disclosure provides a cosmetic composition for preventing or improving intrinsic aging, which contains one or more of paeoniflorin or a salt, isomer, hydrate or solvate thereof, and albiflorin or a salt, isomer, hydrate or solvate thereof as an active ingredient.

In the present disclosure, a 'cosmetic composition' includes any article that improves the appearance of human body. The cosmetic composition for preventing or improving intrinsic aging of the present disclosure refers to an article that improves the appearance of human body by inhibiting the negative effect of physiological phenomena on skin, although not being limited thereto.

The cosmetic composition may further contain, in addition to the paeoniflorin or a salt, isomer, hydrate or solvate thereof and the albiflorin or a salt, isomer, hydrate or solvate thereof, an adjuvant commonly used in a cosmetic composition, such as an antioxidant, a stabilizer, a solubilizer, a vitamin, a pigment, a flavor, etc. and a carrier. For example, the cosmetic composition may further contain an adjuvant such as glycerin, butylene glycol, polyoxyethylene hydrogenated castor oil, tocopheryl acetate, citric acid, panthenol, squalane, sodium citrate, allantoin, etc. The content (unit: wt %) of the active ingredient in the cosmetic composition may be 0.000001 or higher, 0.000005 or higher, 0.00001 or higher, 0.00005 or higher, 0.0001 or higher, 0.0005 or higher, 0.001 or higher, 0.005 or higher, 0.01 or higher, 0.05 or higher, 0.1 or higher or 0.5 or higher, and 1 or lower, 2 or lower, 3 or lower, 4 or lower, 5 or lower, 6 or lower, 7 or lower, 8 or lower, 9 or lower or 10 or lower, specifically 0.000001-10 wt %, more specifically 0.000001-1 wt %, most specifically 0.00001 wt %, based on the total weight of the composition, although not being limited thereto. In an exemplary embodiment, the active ingredient is one or more of paeoniflorin or a salt, isomer, hydrate or solvate thereof, and albiflorin or a salt, isomer, hydrate or solvate thereof. Since the cosmetic composition is applied basically onto skin, it may be prepared into any formulation common in the art. For example, it may be formulated into a solution, a suspension, an emulsion, a paste, a gel, a cream, a lotion, a powder, a soap, a surfactant-containing cleanser, an oil, a powder foundation, an emulsion foundation, a wax foundation, a spray, etc., although not being limited thereto. More specifically, it may be formulated into a softening lotion, a nourishing lotion, a nourishing cream, a massage cream, an essence, an eye cream, a cleansing cream, a cleansing foam, a cleansing water, a mask pack, a spray or a powder.

When the formulation of the present disclosure is a paste, a cream or a gel, an animal oil, a plant oil, a wax, paraffin, starch, tragacanth, a cellulose derivative, polyethylene glycol, silicone, bentonite, silica, talc, zinc oxide, etc. may be contained as a carrier ingredient.

When the formulation of the present disclosure is a powder or a spray, lactose, talc, silica, aluminum hydroxide, calcium silicate, polyamide powder, etc. may be contained as a carrier ingredient. Particularly, a spray may further contain a propellant such as chlorofluorohydrocarbon, propane/butane, dimethyl ether, etc.

When the formulation of the present disclosure is a solution or an emulsion, a solvent, a solubilizer, an emulsifier, etc. may be contained as a carrier ingredient. Specifically, water, ethanol, isopropanol, ethyl carbonate, ethyl acetate, benzyl alcohol, benzyl benzoate, propylene glycol, 1,3-butylene glycol, a glycerol aliphatic ester, polyethylene glycol, a fatty acid ester of sorbitan, etc. may be contained.

When the formulation of the present disclosure is a suspension, a liquid diluent such as water, ethanol, propylene glycol, etc.; a suspending agent such as ethoxylated isostearyl alcohol, polyoxyethylene sorbitol ester, polyoxyethylene sorbitan ester, etc.; microcrystalline cellulose, aluminum metahydroxide, bentonite, agar, tragacanth, etc. may be contained as a carrier ingredient.

When the formulation of the present disclosure is a surfactant-containing cleanser, an aliphatic alcohol sulfate, an aliphatic alcohol ether sulfate, sulfosuccinic acid monoester, isethionate, an imidazolinium derivative, methyl taurate, sarcosinate, a fatty acid amide ether sulfate, an amidoalkyl betaine, an aliphatic alcohol, a fatty acid glyceride, a fatty acid diethanolamide, a plant oil, a lanolin derivative, an ethoxylated glycerol fatty acid ester, etc. may be contained as a carrier ingredient.

In another aspect, the present disclosure provides a functional health food composition for preventing or improving intrinsic aging, which contains one or more of paeoniflorin or a salt, isomer, hydrate or solvate thereof, and albiflorin or a salt, isomer, hydrate or solvate thereof as an active ingredient.

In the present disclosure, a 'functional health food' refers to a food to which special function is added to by physical, biochemical or bioengineering techniques or a processed food designed to sufficiently exhibit a modulatory function relevant to biodefense rhythm control, disease prevention and recovery, etc. It should be unharmful to the human body after long-term intake.

The functional health food may contain a sitologically acceptable supplementary food additive and may further contain a suitable carrier, excipient or diluent commonly used for preparation of functional health food.

When the functional health food composition is used as a food additive, the composition may be added per se or may be used together with other foods or food ingredients according to a common method. The mixing amount of the active ingredient may be determined adequately according to the purpose of use (prevention, health improvement or therapeutic treatment). In general, the content (unit: wt %) of the active ingredient in the food composition may be 0.000001 or higher, 0.000005 or higher, 0.00001 or higher, 0.00005 or higher, 0.0001 or higher, 0.0005 or higher, 0.001 or higher, 0.005 or higher, 0.01 or higher, 0.05 or higher, 0.1 or higher or 0.5 or higher, and 1 or lower, 2 or lower, 3 or lower, 4 or lower, 5 or lower, 6 or lower, 7 or lower, 8 or lower, 9 or lower or 10 or lower, specifically 0.000001-10 wt %, more specifically 0.000001-1 wt %, most specifically 0.00001 wt %, based on the total weight of the composition, although not being limited thereto. In an exemplary embodiment, the active ingredient is one or more of paeoniflorin or a salt, isomer, hydrate or solvate thereof, and albiflorin or a salt, isomer, hydrate or solvate thereof. In case of long-term intake for the purpose of health and hygiene or for the purpose of health management, the content of the active ingredient may be lower than the above-described ranges. Since the active ingredient has no problem in terms of safety, it can also be used in higher contents than the above-described ranges.

The type of the functional health food is not specially limited. Examples of the functional health food containing the active ingredient include dairy products such as ice cream, soups, beverages, tea, drinks, alcoholic beverages, vitamin supplements, etc., and a food to which special function is added or a food designed to sufficiently exhibit a modulatory function relevant to biodefense rhythm control, disease prevention and recovery, etc. are included.

In addition, the functional health food composition according to the present disclosure may contain various kinds of nutritional supplements, vitamins, electrolytes, flavors, colorants, pectic acid and its salts, alginic acid and its salts, organic acids, protective colloidal thickeners, pH control agents, stabilizers, antiseptics, glycerin, alcohols, carbonating agents used in carbonated beverages, etc. In addition, the food composition of the present disclosure may contain a pulp for preparing natural fruit juice, fruit juice drinks or vegetable drinks. These ingredients may be used either independently or in combination. Although the proportion of these additives is of no great importance, they are generally contained in an amount of 0.01-0.1 parts by weight based on 100 parts by weight of the composition of the present disclosure.

In the foregoing description, description of the matter described already above was omitted to avoid unnecessary repetition. And, the terms not defined in the present disclosure have the meanings commonly understood in the technical field to which the present disclosure belongs.

Hereinafter, the present disclosure will be described in detail through examples and comparative examples. However, the following examples and comparative examples are for illustrative purposes only and the scope of the present disclosure is not limited by the examples and comparative examples.

Example 1. Investigation of MMP-1 Inhibition Effect by Paeoniflorin or Albiflorin (Stimulation Source: TNF-α)

Fibroblasts acquired from ATCC were transferred to a medium containing 10% (v/v) FBS and were cultured at 37° C. for 24 hours under the condition of 5% $CO_2$. After replacing the medium with a serum-free medium, the cells were cultured for at least 6 hours. Then, after treating with 10 ng/mL TNF-α, as an intrinsic inflammatory factor causing intrinsic aging, and then with 0.1 ppm or 1 ppm paeoniflorin (Sigma-Aldrich), the cells were cultured for 48 hours. 48 hours later, the culture was separated partly and MMP-1 ELISA was conducted according to a method commonly employed in the art. A negative control group was not treated with paeoniflorin, and a positive control group was treated with 2 μM ATRA (all-trans retinoic acid) instead of the paeoniflorin.

Subsequently, the remaining culture was separated partly and cell viability was measured by CCK8 (cell count kit 8) assay according to a method commonly employed in the art. The result was normalized to the result of the MMP-1 ELISA.

Meanwhile, the MMP-1 inhibition effect by albiflorin was investigated in the same manner as the MMP-1 inhibition effect by paeoniflorin, except that the cells were treated with 0.1 ppm or 1 ppm albiflorin (Wako Chemical) instead of the 0.1 ppm or 1 ppm paeoniflorin.

The measured MMP-1 levels are shown in FIG. 1. A result of calculating MMP-1 inhibition (%) with respect to the negative control group is shown in Table 1.

TABLE 1

| Normalized MMP-1 | Non-treated control | Negative control | Positive control | Paeoniflorin (ppm) | | Albiflorin (ppm) | |
|---|---|---|---|---|---|---|---|
| | | | | 0.1 | 1 | 0.1 | 1 |
| Inhibition (%) | — | 0.00 | 48.75 | 69.34 | 66.49 | 63.25 | 59.44 |

As seen from Table 1 and FIG. 1, with respect to the MMP-1 level of the negative control group treated with TNF-α as 100, the test groups treated with paeoniflorin or albiflorin showed an MMP-1 level of about 60%. This means that paeoniflorin or albiflorin has a superior effect of preventing or improving intrinsic aging.

Example 2. Investigation of MMP-1 Inhibition Effect by Combination of Paeoniflorin and Albiflorin (Stimulation Source: TNF-α)

The MMP-1 inhibition effect by a combination of paeoniflorin and albiflorin was investigated in the same manner as the MMP-1 inhibition effect by paeoniflorin, except that the cells were treated with a 10:1 mixture of paeoniflorin and albiflorin (P+A) at 0.1+0.01 ppm or 1+0.1 ppm instead of the 0.1 ppm or 1 ppm paeoniflorin.

Figure 2:
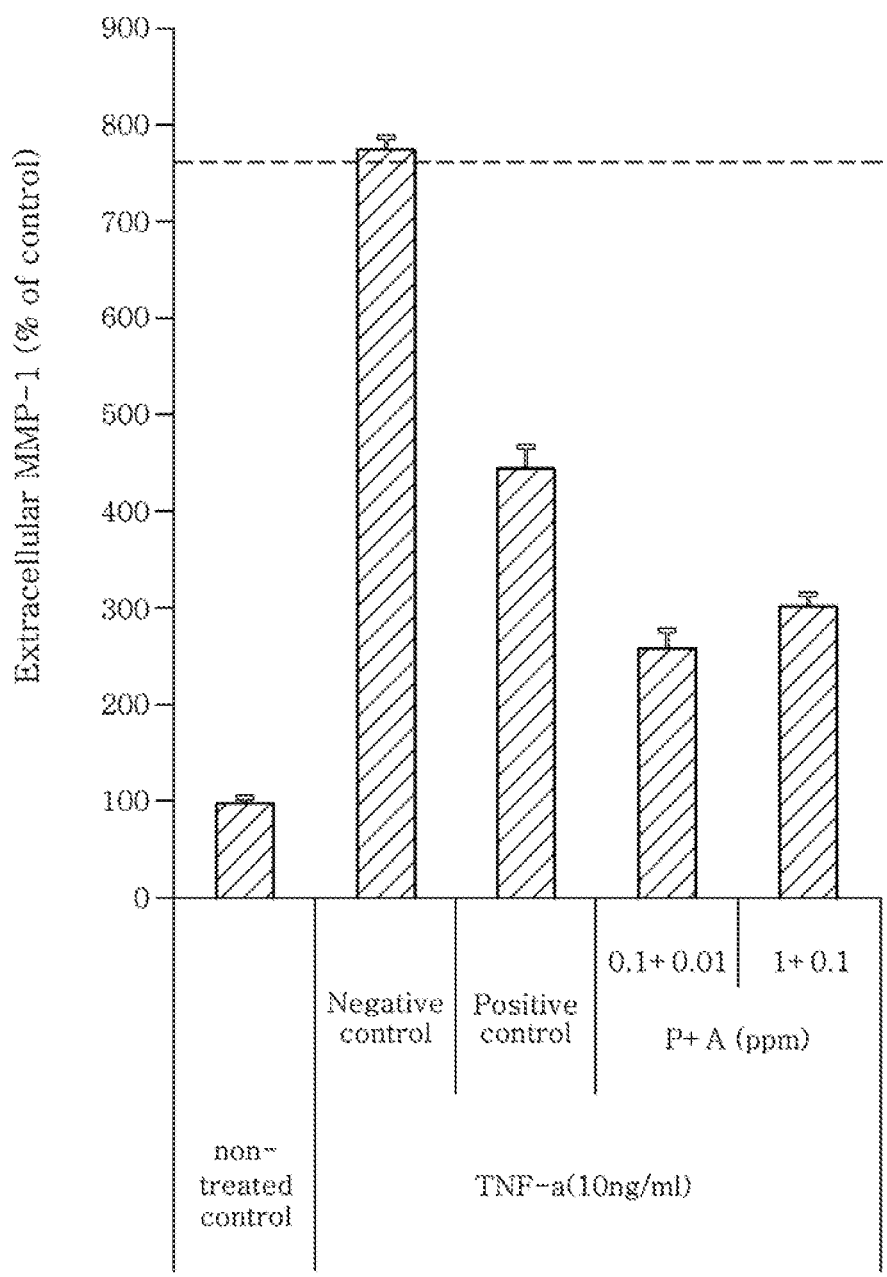
FIG. 2 shows a result of investigating the MMP-1 inhibition effect by a combination of paeoniflorin and albiflorin by using TNF-α as a stimulation source.

The measured MMP-1 levels are shown in FIG. 2. A result of calculating MMP-1 inhibition (%) with respect to the negative control group is shown in Table 2.

TABLE 2

| Normalized MMP-1 | Non-treated control | Negative control | Positive control | Paeoniflorin + albiflorin (ppm) | |
|---|---|---|---|---|---|
| | | | | 0.1 + 0.01 | 1 + 0.1 |
| Inhibition (%) | — | 0.00 | 48.75 | 76.67 | 70.02 |

As seen from Table 2 and FIG. 2, when the cells were treated with a mixture of paeoniflorin and albiflorin, the MMP-1 inhibition was higher than 70%, specifically 70.02% and 76.67%, respectively. These inhibition rates are significantly higher than those obtained in Example 1 with paeoniflorin or albiflorin alone. This result means that a combination of paeoniflorin and albiflorin has a remarkable effect of preventing or improving intrinsic aging.

Comparative Example 1. Investigation of MMP-1 Inhibition Effect by Paeoniflorin or Albiflorin (Stimulation Source: UV)

Fibroblasts acquired from ATCC were transferred to a medium containing 10% (v/v) FBS and were cultured at 37° C. for 24 hours under the condition of 5% $CO_2$. After replacing the medium with a serum-free medium, the cells were cultured for at least 6 hours. Then, after treating with 30 $mJ/cm^2$ UVB, as an extrinsic stimulating factor causing extrinsic aging, and then with 0.1 ppm or 1 ppm paeoniflorin (Sigma-Aldrich), the cells were cultured for 48 hours. 48 hours later, the culture was separated partly and MMP-1 ELISA was conducted according to a method commonly employed in the art. A negative control group was not treated with paeoniflorin, and a positive control group was treated with 2 μM ATRA (all-trans retinoic acid) instead of the paeoniflorin.

Subsequently, the remaining culture was separated partly and cell viability was measured by CCK8 (cell count kit 8) assay according to a method commonly employed in the art. The result was normalized to the result of the MMP-1 ELISA.

Meanwhile, the MMP-1 inhibition effect by albiflorin was investigated in the same manner as the MMP-1 inhibition effect by paeoniflorin, except that the cells were treated with 0.1 ppm or 1 ppm albiflorin (Wako Chemical) instead of the 0.1 ppm or 1 ppm paeoniflorin.

Figure 3:
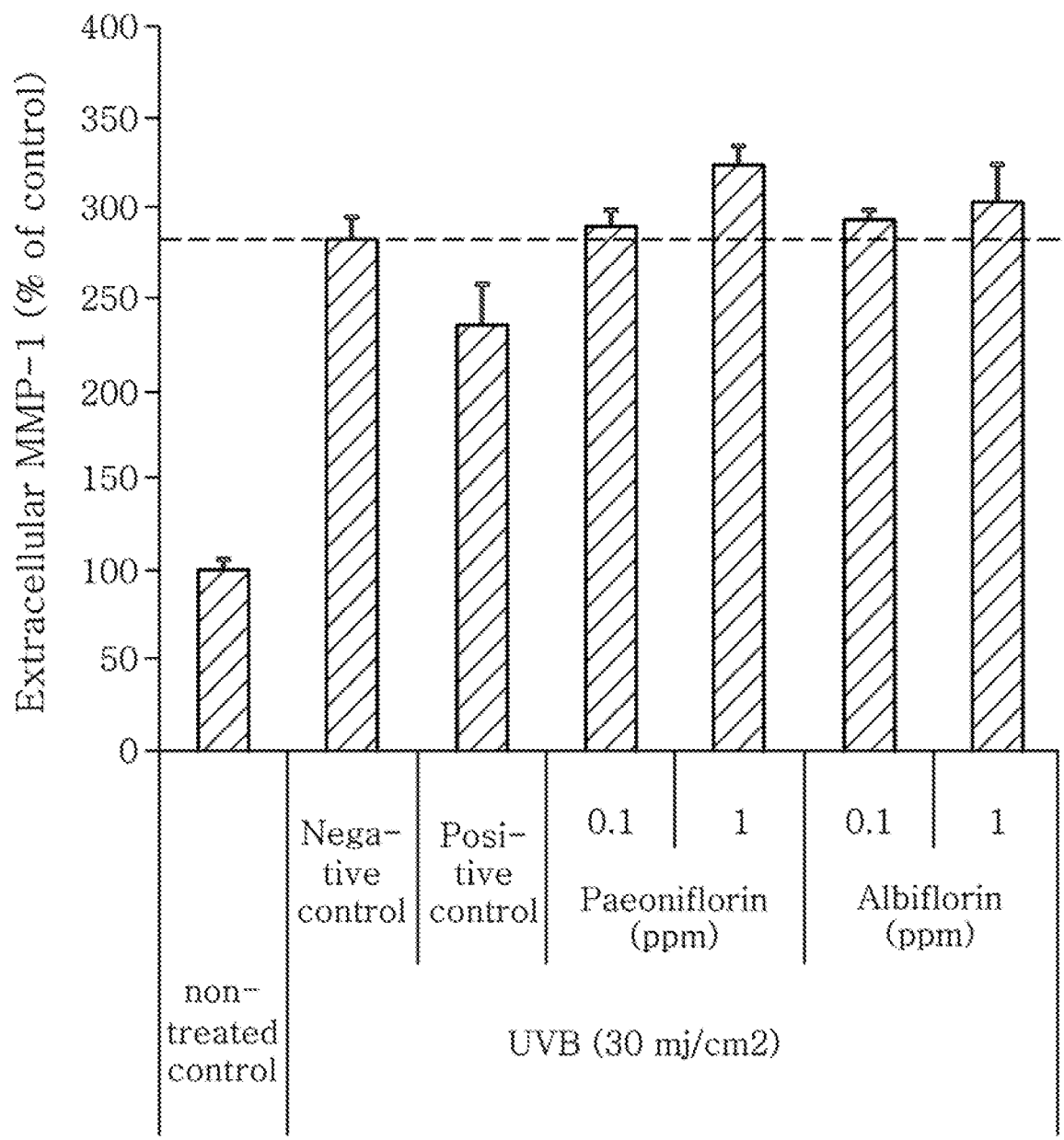
FIG. 3 shows a result of investigating the MMP-1 inhibition effect by paeoniflorin or albiflorin by using UV as a stimulation source.

The measured MMP-1 levels are shown in FIG. 3. A result of calculating MMP-1 inhibition (%) with respect to the negative control group is shown in Table 3.

TABLE 3

| Normalized MMP-1 | Non-treated | Negative control | Positive control | Paeoniflorin (ppm) | | Albiflorin (ppm) | |
|---|---|---|---|---|---|---|---|
| | | | | 0.1 | 1 | 0.1 | 1 |
| Inhibition (%) | — | 0.00 | 25.72 | -3.27 | -22.03 | -5.29 | -10.96 |

As seen from Table 3 and FIG. 3, when the positive control group was treated with ATRA and the test groups were treated with paeoniflorin or albiflorin, the MMP-1 level was increased for the test groups treated with paeoniflorin or albiflorin as compared to the positive control group. The MMP-1 level was increased up to about 22.03% when compared with the negative control group. This result suggests that paeoniflorin or albiflorin has no effect on photoaging, which is a type of extrinsic aging, whereas it exhibits a specific effect on intrinsic aging.

Hereinafter, the present disclosure will be described in detail through formulation examples. However, the following formulation examples are for illustrative purposes only and the scope of the present disclosure is not limited by them.

Formulation Example 1. Preparation of Cosmetic Formulations 1-1. Preparation of Softening Lotion A softening lotion was prepared according to a common method by mixing 0.1 wt % of paeoniflorin or albiflorin, 5.2 wt % of 1,3-butylene glycol, 1.5 wt % of oleyl alcohol, 3.2 wt % of ethanol, 3.2 wt % of polysorbate 20, 2.0 wt % of benzophenone-9, 1.0 wt % of carboxyvinyl polymer, 3.5 wt % of glycerin, a trace amount of flavor, a trace amount of antiseptic, and purified water as balance.

1-2. Preparation of Milk Lotion

A milk lotion was prepared according to a common method by mixing 0.1 wt % of paeoniflorin or albiflorin, 5.1 wt % of glycerin, 4.2 wt % of propylene glycol, 3.0 wt % of tocopheryl acetate, 4.6 wt % of liquid paraffin, 1.0 wt % of triethanolamine, 3.1 wt % of squalane, 2.5 wt % of macadamia nut oil, 1.6 wt % of polysorbate 60, 1.6 wt % of sorbitan sesquioleate, 0.6 wt % of propylparaben, 1.5 wt % of carboxyvinyl polymer, a trace amount of flavor, a trace amount of antiseptic, and purified water as balance.

1-3. Preparation of Nourishing Cream

A nourishing cream was prepared according to a common method by mixing 0.5 wt % of paeoniflorin or albiflorin, 4.0 wt % of glycerin, 3.5 wt % of vaseline, 2.1 wt % of triethanolamine, 5.3 wt % of liquid paraffin, 3.0 wt % of squalane, 2.6 wt % of beeswax, 5.4 wt % of tocopheryl acetate, 3.2 wt % of polysorbate 60, 1.0 wt % of carboxyvinyl polymer, 3.1 wt % of sorbitan sesquioleate, a trace amount of flavor, a trace amount of antiseptic, and purified water as balance.

1-4. Preparation of Massage Cream

A massage cream was prepared according to a common method by mixing 0.5 wt % of paeoniflorin or albiflorin, 4.0 wt % of glycerin, 3.5 wt % of vaseline, 0.5 wt % of triethanolamine, 24.0 wt % of liquid paraffin, 3.0 wt % of squalane, 2.1 wt % of beeswax, 0.1 wt % of tocopheryl acetate, 2.4 wt % of polysorbate 60, 1.0 wt % of carboxyvinyl polymer, 2.3 wt % of sorbitan sesquioleate, a trace amount of flavor, a trace amount of antiseptic, and purified water as balance.

1-5. Preparation of Body Cleanser

A body cleanser was prepared according to a common method by mixing 1 g of paeoniflorin or albiflorin, 18 g of an anionic surfactant, 5 g of a non-ionic surfactant, 7 g of glycerin, 3 g of sodium chloride, 1.5 g of natural olive oil liquid soap, 1 g of a flavor, and 100 g of water.

Formulation Example 2. Preparation of Food Formulations 2-1. Preparation of Health Food A health food was prepared according to a common method by mixing 100 mg of paeoniflorin or albiflorin, an adequate amount of a vitamin mixture (70 g of vitamin A acetate, 1.0 mg of vitamin E, 0.13 mg of vitamin $B_1$, 0.15 mg of vitamin $B_2$, 0.5 mg of vitamin $B_6$, 0.2 g of vitamin $B_{12}$, 10 mg of vitamin C, 10 g of biotin, 1.7 mg of nicotinamide, 50 g of folic acid, 0.5 mg of calcium pantothenate), and an adequate amount of a mineral mixture (1.75 mg of ferrous sulfate, 0.82 mg of zinc oxide, 25.3 mg of magnesium carbonate, 15 mg of monopotassium phosphate, 55 mg of dicalcium phosphate, 90 mg of potassium citrate, 100 mg of calcium carbonate, 24.8 mg of magnesium chloride) and preparing the mixture into a granule.

The above-described compositions of the vitamin and mineral mixtures are given as relatively preferred examples for health food but may be varied as desired.

2-2. Preparation of Health Drink

According to a common health drink preparation method, 100 mg of paeoniflorin or albiflorin, 15 g of vitamin C, 100 g of vitamin E (powdered), 19.75 g of iron lactate, 3.5 g of zinc oxide, 3.5 g of nicotinamide, 0.2 g of vitamin A, 0.25 g of vitamin $B_1$, 0.3 g of vitamin $B_2$, and a suitable amount of water were mixed. The resulting solution was heated with agitation at 85° C. for about 1 hour and then filtered. The filtered solution was filled in a sterilized 2-L vessel and then stored in a refrigerator after sealing and sterilization.

The above-described composition illustrates a preferable example relatively suitable for a health drink. However, it can be modified as desired according to regional and ethnic preferences such as particular consumers, countries, purpose of use, etc.

The invention claimed is:

1. A method for improving intrinsic aging, comprising administering a composition comprising:
   isolated paeoniflorin or a salt, isomer, hydrate or solvate thereof, and
   isolated albiflorin or a salt, isomer, hydrate or solvate thereof to a subject in need thereof,
   wherein the albiflorin or a salt, isomer, hydrate or solvate thereof is comprised in an amount of 1-30 parts by weight based on 100 parts by weight of the paeoniflorin or a salt, isomer, hydrate or solvate thereof.

2. The method for improving intrinsic aging according to claim 1, wherein the intrinsic aging is aging caused by intrinsic inflammation.

3. The method for improving intrinsic aging according to claim 1, wherein the intrinsic aging is aging caused by TNF-α.

4. The method for improving intrinsic aging according to claim 1, wherein the improvement of intrinsic aging is achieved by MMP-1 inhibition.

5. The method for improving intrinsic aging according to claim 1, wherein the composition is a cosmetic composition.

6. The method for improving intrinsic aging according to claim 1, wherein the composition is a functional health food composition.

* * * * *